United States Patent [19]

Breitenbucher et al.

[11] Patent Number: 5,573,984
[45] Date of Patent: Nov. 12, 1996

[54] POROUS BODY FOR THE STORAGE AND REGULATED RELEASE OF VAPORIZABLE SUBSTANCES

[75] Inventors: Klaus Breitenbücher, Nackenheim; Hermann Schuster, Taunusstein, both of Germany

[73] Assignee: Schott Glaswerke, Mainz, Germany

[21] Appl. No.: 445,729

[22] Filed: May 22, 1995

[30] Foreign Application Priority Data

May 20, 1994 [DE] Germany .......................... 44 17 739.9

[51] Int. Cl.$^6$ ....................................... A61L 9/12
[52] U.S. Cl. ..................... 501/39; 261/94; 261/DIG. 4
[58] Field of Search ................................ 501/39; 261/94, 261/DIG. 17

[56] References Cited

U.S. PATENT DOCUMENTS

| 4,588,540 | 5/1986 | Kiefer et al. | 264/43 |
| 4,788,164 | 11/1988 | Che et al. | 501/39 |
| 4,987,068 | 1/1991 | Trösch et al. | 435/41 |

FOREIGN PATENT DOCUMENTS

| 2591115 | 6/1987 | France . |
| 1236343 | 6/1971 | United Kingdom . |
| 2194889 | 3/1988 | United Kingdom . |

OTHER PUBLICATIONS

Abstract, Week 8404, JP 84–021483, Derwent Publications Ltd., GB; AN 84–021483, 12 Dec. 1983.
Derwent Abstract 84–021483, Dec. 12, 1983.

*Primary Examiner*—Melissa Bonner
*Attorney, Agent, or Firm*—Millen, White, Zelano & Branigan, P.C.

[57] ABSTRACT

There is described a porous body for the storage and regulated release of vaporizable substances, which consists of open-pored sintered glass. The body preferably has a pore volume of from 30% to 85% and a mean pore size of from 10 to 350 μm. The body is inert to the stored substances, has a very high storage volume and releases the stored substances very uniformly, and in particular, with no chromatography effects occurring.

12 Claims, No Drawings

POROUS BODY FOR THE STORAGE AND REGULATED RELEASE OF VAPORIZABLE SUBSTANCES

BACKGROUND OF THE INVENTION

This invention relates to porous glass bodies and to a method of storing volatile substances in such bodies so as to permit a regulated evolution of such substances.

In industry, in the household and in hospitals, in agriculture and forestry and in the interior of vehicles, there is wide use of devices which emit gaseous fragrances or active compounds serving, for example, as air fresheners, insecticides or insect-attractants (by release of pheromones).

All of these fragrance or active-compound emitters have in common that by evaporation or sublimation, they are supposed to release the fragrances or active compounds over a prolonged period of time as uniformly as possible with the concentration remaining the same and the composition being unaltered. The period of time over which the fragrances or active compounds are to be released is, in the case of fragrances for air freshening purposes, generally about 4–8 weeks, and in the case of active compounds such as insecticides it may be a number of months.

Carrier media used heretofore have considerable disadvantages including the fact that the release of the stored substance is often too fast or too slow. For example, a widely used device utilizes a cellulose membrane which closes off a container containing the fragrance. Such membranes have no defined pore structure so that the release of material can be controlled only with difficulty. In the case of fluctuating air movements, the membrane can dry out very quickly; the supply of stored material then stagnates. Furthermore, an aged membrane has a selective action so that the entire range of active compounds is no longer liberated, i.e. the composition of the active compounds changes with time.

A simpler way of storing and releasing fragrances and active compounds is the use of porous bodies in which the fragrance or active compound is located in the pores of the porous body and is vaporized therefrom.

Porous ceramic bodies, for example those produced by Rauschert Verfahrenstcelnick of Steinwiesen, Germany, in general, have relatively low total pore volumes of up to about 50% of the sintered body, with the volume of open pores being up to about 44% of the sintered body. Thus, the materials to be vaporized can be stored internally to only a limited extent so that only relatively small amounts of vaporizable material can be released per unit volume. Another disadvantage of ceramics is that the mineral materials unavoidably present in ceramics can lead to the selective fixing and thus separation of scents.

Other inexpensive materials which are frequently used as carriers are entire bodies of cellulose fibers, in particular cellulose felts or nonwovens. These bodies have no defined pore structure and, as a result of their fibrous structures, reduce the action of the capillary forces. The numerous hydroxyl groups of cellulose, by virtue of their interaction with polar groups of the fragrances or active compounds and with water molecules, lead to an undesired and nonuniformly strong fixing of active compounds and scents which can occur even during storage, as well as to undesired chromatographic effects occurring during the release of active compounds. Owing to these phenomena, especially in the case of highly active compounds and scents or mixtures of materials, the desired consistency of performance is impaired, for example, shifts in the fragrance in comparison with the non-adsorbed original material.

A further disadvantage of the cellulose bodies is their swellability. Under relatively high atmospheric humidity, the cellulose body can break up in layers and the excessive access of air which follows reduces the time of evolution and alters the desired concentration of active compound in the air of the room. In use, the cellulose bodies can also suffer deformation and discoloration, which adversely affects the aesthetic and sales values of products using these carriers.

SUMMARY OF THE INVENTION

One object of this invention to provide a porous body suitable for the storage and regulated release of vaporizable substances (fragrance or active-compound emitter), which in comparison to its volume can store a large amount of substance, which is inert to the substance to be stored and which ensures uniform or substantially uniform vaporization of the stored substance in a composition unaltered in comparison with the pure substance over a long period of time.

Another object is to provide articles combining the porous body with a fragrance and/or an insecticide and/or a pheromone.

Upon further study of the specification and appended claims, further objects and advantages of this invention will be apparent to those skilled in the art.

To achieve these objects, there is provided as the porous body, an open-pored sintered glass which has been found to be exceptionally suitable as a body for the storage and regulated release of vaporizable substances.

Glass is largely chemical resistant and does not react with conventional fragrances and active compounds. For most applications, bodies of simple lime-soda glass are most suitable, whereas for higher requirements of chemical resistance there can be used borosilicate glass from which most laboratory apparatus is also made (e.g. borosilicate glass 3.3). Such borosilicate bodies can also be used to store certain active compounds which could not be satisfactorily stored in the conventional storage media described above.

The composition of lime-soda glass is generally known and is usually, on an oxide basis, within the range 70%–75% by weight of $SiO_2$; 12%–16% by weight of $Na_2O$ (+$K_2O$); 8%–11% by weight of CaO; 2%–5% by weight of MgO and about 1% by weight of $Al_2O_3$.

Borosilicate glass has a composition range (in % by weight on an oxide basis) of about 70–85 $SiO_2$; 5–15 $B_2O_3$; 3–7 alkali metal oxides: 2–5 $Al_2O_3$; 0–4 alkaline earth metal oxides. The two abovementioned types of glass are given only as examples since it is of course also possible to use many other types of glass.

For the storage of the fragrances and active compounds, the body has to be open-pored, since the storage occurs in the pores. Since it is impossible to avoid the presence in the body of scattered closed pores, the term open-pored also includes such a body containing up to 10% of the pore volume as closed pores. Thus, the minimum quantity of open pores is 90%, preferably at least 95%, and optionally about 100%.

The stored fragrance is held in the pores by means of the capillary forces and vaporizes at the surface of the body. The size of the pores influences the vaporization rate. The smaller the pores, the slower is the vaporization. The selection of a suitable pore size can be used to set the vaporization time, i.e. the time until the stored substance is released again, while also taking into account the volatility of the substance to be vaporized. The more volatile a substance, the smaller the pores must be for a given vaporization time. A mean pore size of from 10 to 350 μm has been found to be very suitable, with mean pore sizes in the range from 40 to 100 μm being preferred.

To be able to store as large as possible an amount of substance in the body, the pore volume should be as high as possible. Good results are achieved using bodies in which the pore volume is from 30% to 85% of the body. Below a pore volume of 30%, the amount of substance able to be stored becomes too small for most applications, above 85% the mechanical strength of the bodies becomes increasingly low. Particular preference is given to bodies having pore volumes of from 50% to 85%, especially 50% to 75%, particularly from 55% or 60% to 75%.

The introduction of the fragrance or active compound into the body is carried out, for example, by dripping the liquid active compound or the active compound solution onto the body, and by impregnation of the body with the active compound, or by dipping the body into the active compound or the active compound solution, with the active compound being rapidly distributed within the body as a result of the capillary forces.

Apart from bodies having a very uniform pore size, bodies having a so-called double pore structure are also suitable. The latter bodies contain macropores having a pore size of from 20 to 450 μm with open micropores in the cell walls of the macropores. These micropores have a pore size of from about 1 to 10 μm. At a total pore volume of the body of from 30% to 85%, the pore volume of the macropores is from about 25% to 80% and that of the micropores is from about 5% to 30%. It is contemplated that the double pore structure will provide greater capillary forces which will result in a more rapid absorbance and possibly a slower release as well.

Numerous processes are known for producing the porous bodies, (including those having a double pore structure). One of these processes is described in U.S. Pat. No. 4,588,540. According to this process, glass samples and an inorganic salt are sintered and the salt is leached from the sintered body. Particle size and particle size distribution of salt and glass powder and also the ratio of salt to glass powder determine the properties of the sintered body obtained. Another process is the so-called burn-out process described in Japanese patent document 3- 93-643 A; but this process yields less uniform results compared to the salt process.

The bodies for storing the substances can be provided in any shape. They can be used as cubes, plates, rings or spheres, as rod sections or in a decorative shapes, e.g. heart-shaped, tree-shaped, animal-shaped and the like.

The advantages of the porous body, owing to its high pore volume, are, in particular, that it is able to store a very large amount of fragrances and active compounds in comparison with its volume, that it consists of a material which is inert to the substance being stored, that the release of the material stored is very uniform not only over time but also with respect of the composition of a mixture of materials because chromatographic effects do not occur, and that the period of release of the material can be influenced by the selection of a suitable pore size.

As for the vaporizable materials which are stored in the open-pored glass body, it is contemplated that all vaporizable materials can be used, e.g., fragrances, air freshener compositions, insecticides and pheromones. It would be neither possible nor useful to catalog all such vaporizable materials. For example, perfumes, e.g., apple blossom, morning scent, the Chanel perfumes, etc., known only by their names and not by their trade secret chemical compositions, are mixtures of natural and artificial fragrances. They have been used and stored for centuries in sponges and sachets and the like for slow delivery. Thus, this invention contemplates a combination of the porous body with all vaporizable materials, known not only now, but also those vaporizable materials invented in the future.

Without further elaboration, it is believed that one skilled in the art can, using the preceding description, utilize the present invention to its fullest extent. The following preferred specific embodiment is, therefore, to be construed as merely illustrative, and not limitative of the remainder of the disclosure in any way whatsoever.

The entire disclosures of all applications, patents and publications, cited above and below, and of corresponding German application P 44 17 7 39.9-41, are hereby incorporated by reference.

EXAMPLE

A disc-shaped porous sintered glass body having a diameter of 33 mm and a thickness of 8 mm, which had been produced from a lime-soda glass and possessed a pore volume of 65% and a mean pore size of 70 μm, was impregnated with 3.6 g of a mixture of perfume essences and subsequently exposed to the atmosphere as an air freshener. An almost linear decrease in the concentration of material in the carrier body and an approximately constant concentration of material in the air of the room was found over a period of 5 weeks. The olfactory impression of the vaporized mixture remained virtually unaltered over the entire period.

The preceding example can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A vapor-releasing device comprising a vaporizable liquid stored in an open-pored sintered glass body, wherein at least 90% of the pores are open pores, the glass body posses a pore volume of 30%–85 % and a mean pore size of 10–350 μm, and the vaporizable liquid is a perfume, an air freshener, an insecticide or a pheromone.

2. A device according to claim 1, possessing a pore volume of 50%–75%.

3. A device according to claim 1, possessing a mean pore size of 40–100 μm.

4. A device according to claim 3, possessing a pore volume of 50%–75%.

5. A device according to claim 4, wherein at least 95% of the pores are open pores.

6. A device according to claim 4, wherein at least 95% of the pores are open pores.

7. A device according to claim 4, wherein about 100% of the pores are open pores.

8. A device according to claim 6, wherein the vaporizable liquid is a perfume.

9. A device according to claim 1, wherein the vaporizable liquid is a perfume.

10. A device according to claim 1, wherein the glass is a lime-soda glass or a borosilicate glass.

11. A device according to claim 4, wherein the glass is a lime-soda glass or a borosilicate glass.

12. A device according to claim 6, wherein the glass is a lime-soda glass or a borosilicate glass.

\* \* \* \* \*